United States Patent
Ludwin et al.

(10) Patent No.: US 9,949,664 B2
(45) Date of Patent: Apr. 24, 2018

(54) DETERMINING NON-CONTACT STATE FOR A CATHETER

(71) Applicant: BIOSENSE WEBSTER (ISRAEL) LTD., Yokneam (IL)

(72) Inventors: Doron Moshe Ludwin, Haifa (IL); Aharon Turgeman, Zichron Ya'acov (IL); Natan Sharon Katz, Kiryat Bialik (IL); Erez Silberschein, Tel Aviv (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 549 days.

(21) Appl. No.: 14/010,697

(22) Filed: Aug. 27, 2013

(65) Prior Publication Data

US 2015/0065851 A1 Mar. 5, 2015

(51) Int. Cl.
*A61B 5/103* (2006.01)
*A61B 5/06* (2006.01)
(Continued)

(52) U.S. Cl.
CPC ............ *A61B 5/062* (2013.01); *A61B 5/0538* (2013.01); *A61B 5/068* (2013.01); *A61B 5/1076* (2013.01);
(Continued)

(58) Field of Classification Search
CPC ...... A61B 18/1492; A61B 2018/00357; A61B 2019/5251; A61B 2019/465;
(Continued)

(56) References Cited

U.S. PATENT DOCUMENTS 6,226,542 B1  5/2001  Reisfeld
6,241,724 B1  6/2001  Fleischman et al.
(Continued)

FOREIGN PATENT DOCUMENTS

CN  102551876 A  7/2012
CN  102599911 A  7/2012
(Continued)

OTHER PUBLICATIONS

European Search Report for European Application No. 14182271.8, dated Jan. 23, 2015.
(Continued)

*Primary Examiner* — Elmer Chao
(74) *Attorney, Agent, or Firm* — Dergosits & Noah LLP; Todd A. Noah (57) ABSTRACT

A method, including inserting a probe into a cavity in a subject's body and receiving, from a force sensor in the probe, first readings indicative of a first change in measured contact forces between the probe and the cavity by less than a predetermined limit over at least a predetermined interval of time. The method continues by receiving second readings from the force sensor when the second readings have changed by more than a predetermined force threshold or location coordinates of the probe have changed by at least a predetermined location change threshold. The method continues by receiving third readings indicative of a second change in the measured contact forces between the probe and the cavity by less than the predetermined limit over at least the predetermined interval of time. The method concludes by calibrating a zero-force point for the force sensor according to the third readings.

14 Claims, 4 Drawing Sheets

(51) Int. Cl.
  *A61B 5/00* (2006.01)
  *A61B 18/14* (2006.01)
  *A61B 5/053* (2006.01)
  *A61B 5/107* (2006.01)
  *A61B 17/00* (2006.01)
  *A61B 90/00* (2016.01)
  *A61B 34/20* (2016.01)

(52) U.S. Cl.
  CPC .......... *A61B 5/4836* (2013.01); *A61B 5/6885* (2013.01); *A61B 18/1492* (2013.01); *A61B 2017/00725* (2013.01); *A61B 2034/2051* (2016.02); *A61B 2090/065* (2016.02); *A61B 2505/05* (2013.01); *A61B 2560/0223* (2013.01)

(58) Field of Classification Search
  CPC .......... A61B 2019/464; A61B 2505/05; A61B 2090/065; A61B 2034/2051
  See application file for complete search history.

(56) References Cited

U.S. PATENT DOCUMENTS

| | | | |
|---|---|---|---|
| 6,301,496 | B1 | 10/2001 | Reisfeld |
| 6,695,808 | B2 | 2/2004 | Tom |
| 6,892,091 | B1 | 5/2005 | Ben Haim |
| 6,915,149 | B2 | 7/2005 | Ben-Haim |
| 7,306,593 | B2 | 12/2007 | Keidar et al. |
| 7,497,858 | B2 | 3/2009 | Chapelon |
| 7,536,218 | B2 | 5/2009 | Govari |
| 2007/0100332 | A1 | 5/2007 | Paul et al. |
| 2008/0275465 | A1 | 11/2008 | Paul et al. |
| 2008/0288038 | A1 | 11/2008 | Paul et al. |
| 2009/0093806 | A1 | 4/2009 | Govari et al. |
| 2012/0108988 | A1* | 5/2012 | Ludwin .............. A61B 18/1492 600/508 |

FOREIGN PATENT DOCUMENTS

| | | |
|---|---|---|
| CN | 102835965 A | 12/2012 |
| EP | 2449996 A2 | 5/2012 |
| EP | 2462869 A1 | 6/2012 |
| EP | 2529667 A2 | 12/2012 |
| EP | 2537551 A1 | 12/2012 |
| EP | 2574278 A2 | 4/2013 |
| WO | 07/098494 A1 | 8/2007 |

OTHER PUBLICATIONS

China Search Report for Chinese Application No. 2014104292066, dated Nov. 11, 2017.

* cited by examiner

DETERMINING NON-CONTACT STATE FOR A CATHETER

CROSS-REFERENCE TO RELATED APPLICATION

This application is related to U.S. patent application titled "Determining Absence of Contact for a Catheter," filed on even date with the present application, and which is incorporated herein by reference.

FIELD OF THE INVENTION

The present invention relates generally to contact determination, and specifically to determination of absence of contact of a catheter with body tissue.

BACKGROUND OF THE INVENTION

In an ablation procedure on target tissue, such as the myocardium, verification of physical electrode contact with the target tissue, as well as measurement of the force or pressure of the contact, are important for controlling the delivery of ablation energy to the tissue. Attempts in the art to verify electrode contact with the tissue, and to accurately measure the contact force, have been extensive, and various techniques have been suggested. For example, U.S. Pat. No. 6,695,808, which is incorporated herein by reference, describes apparatus for treating a selected patient tissue or organ region. A probe has a contact surface that may be urged against the region, thereby creating contact pressure. A pressure transducer measures the contact pressure. This arrangement is said to meet the needs of procedures in which a medical instrument must be placed in firm but not excessive contact with an anatomical surface, by providing information to the user of the instrument that is indicative of the existence and magnitude of the contact force.

As another example, U.S. Pat. No. 6,241,724, which is incorporated herein by reference, describes methods for creating lesions in body tissue using segmented electrode assemblies. In one embodiment, an electrode assembly on a catheter carries pressure transducers, which sense contact with tissue and convey signals to a pressure contact module. The module identifies the electrode elements that are associated with the pressure transducer signals and directs an energy generator to convey RF energy to these elements, and not to other elements that are in contact only with blood.

A further example is presented in U.S. Pat. No. 6,915,149, which is incorporated herein by reference. This patent describes a method for mapping a heart using a catheter having a tip electrode for measuring local electrical activity. In order to avoid artifacts that may arise from poor tip contact with the tissue, the contact pressure between the tip and the tissue is measured using a pressure sensor to ensure stable contact.

U.S. Patent Application Publication 2007/0100332, which is incorporated herein by reference, describes systems and methods for assessing electrode-tissue contact for tissue ablation. An electro-mechanical sensor within the catheter shaft generates electrical signals corresponding to the amount of movement of the electrode within a distal portion of the catheter shaft. An output device receives the electrical signals for assessing a level of contact between the electrode and a tissue.

U.S. Pat. No. 7,306,593, issued to Keidar et al., which is incorporated herein by reference, describes a method for ablating tissue in an organ by contacting a probe inside the body with the tissue to be ablated, and measuring one or more local parameters at the contact position using the probe prior to ablating the tissue. A map of the organ is displayed, showing, based on the one or more local parameters, a predicted extent of ablation of the tissue to be achieved for a given dosage of energy applied at the position using the probe. The given dosage of energy is applied to ablate the tissue using the probe, and an actual extent of the ablation at the position is measured using the probe subsequent to ablating the tissue. The measured actual extent of the ablation is displayed on the map for comparison with the predicted extent.

Impedance-based methods for assessing catheter-tissue contact that are known in the art typically rely on measurement of the magnitude of the impedance between an electrode on the catheter and a body-surface electrode. When the magnitude is below some threshold, the electrode is considered to be in contact with the tissue. This sort of binary contact indication may be unreliable, however, and is sensitive to changes in the impedance between the body-surface electrode and the skin.

U.S. Patent Application Publication Nos. 2008/0288038 and 2008/0275465, both by Saurav et al., which are incorporated herein by reference, describe an electrode catheter system having an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides a method, including:

inserting a probe into a cavity in a body of a subject;

receiving, in a first period, from a force sensor in the probe, first readings indicative of a first change in measured contact forces between the probe and the cavity by less than a predetermined limit over at least a predetermined interval of time;

receiving, in a second period after the first period, second readings from the force sensor when one condition is met from a set of conditions consisting of:

the second readings having changed by more than a predetermined force threshold in the second period; and location coordinates of the probe having changed by at least a predetermined location change threshold in the second period;

receiving from the force sensor, in a third period after the second period, third readings indicative of a second change in the measured contact forces between the probe and the cavity by less than the predetermined limit over at least the predetermined interval of time; and calibrating a zero-force point for the force sensor according to the third readings.

In a disclosed embodiment the method includes:

receiving in the first period first location signals indicative of a first location change for the probe by more than a predetermined location threshold; and receiving in the third period second location signals indicative of a second location change for the probe by more than the predetermined location threshold.

The measured contact forces may include magnitudes of the contact forces. Alternatively or additionally the measured contact forces may include directions of contact forces.

In a further disclosed embodiment the probe consists of a first probe, and the method further includes:

inserting a second probe into the cavity in proximity to the first probe;

receiving in the first period first signals indicative of a first change in a measured value of the proximity by less than a predetermined proximity change threshold; and receiving in the third period second signals indicative of a second change in the measured value of the proximity by less than the predetermined proximity change threshold.

The method may yet further include receiving the first signals and the second signals from the force sensor.

In an alternative embodiment the probe includes a magnetic field sensor, the method further including measuring the location coordinates of the probe in response to magnetic fields sensed by the sensor.

In a further alternative embodiment the probe includes an electrode, the method further including measuring the location coordinates in response to an impedance of current flowing through the electrode.

Typically, the predetermined limit of the measured contact forces is equal to the predetermined force threshold.

There is further provided, according to an embodiment of the present invention, apparatus, including:

a probe configured to be inserted into a cavity in a body of a subject;

a force sensor located within the probe; and a processor, configured;

to receive from the force sensor, in a first period, first readings indicative of a first change in measured contact forces between the probe and the cavity by less than a predetermined limit over at least a predetermined interval of time, to receive, in a second period after the first period, second readings from the force sensor when one condition is met from a set of conditions consisting of:

the second readings having changed by more than a predetermined force threshold in the second period, and location coordinates of the probe having changed by at least a predetermined location change threshold in the second period, to receive from the force sensor, in a third period after the second period, third readings indicative of a second change in the measured contact forces between the probe and the cavity by less than the predetermined limit over at least the predetermined interval of time, and to calibrate a zero-force point for the force sensor according to the third readings.

The present disclosure will be more fully understood from the following detailed description of the embodiments thereof, taken together with the drawings, in which:

DETAILED DESCRIPTION OF EMBODIMENTS

OVERVIEW

In a medical ablation procedure, such as ablation of heart tissue, it is extremely useful to be able to measure the force applied (to the tissue) while the tissue is being ablated. This is because the force applied is a key parameter governing the amount of tissue ablated for a given ablation energy input to the tissue. The ablation is typically provided by a probe comprising an ablation electrode at its distal end. To measure the force a force sensor may be incorporated into the distal end, but such force sensors known in the art typically drift, i.e., even if the force exerted on the sensor is constant, readings from the sensor change. Such drift may be compensated for by zeroing the sensor periodically, typically before applying ablation energy. However, the zeroing of the sensor should only be applied if the sensor is not contacting tissue, i.e., the sensor is in a state where the force on it is effectively zero (such a state is typically achieved if the sensor is surrounded by blood in the heart chamber, and is not contacting a heart wall).

Embodiments of the present invention detect such a state for the sensor, herein termed a zeroing state. The force sensor is assumed to be in a zeroing state if over at least a predetermined interval of time force readings from the sensor change by less than a predetermined force limit. To ensure that the sensor is in the zeroing state, the probe having the force sensor is typically also assumed to change its location during the predetermined time interval by more than a predetermined location threshold.

In addition to detecting a zeroing state for the sensor, embodiments of the present invention auto-zero the sensor, i.e., they calibrate a zero-force point for the force sensor. In order to auto-zero the sensor, received signals from the sensor are checked to detect a situation wherein the sensor is in a first zeroing state, then in a non-zeroing state (such as if the sensor indicates it is touching tissue), and then in a second zeroing state. Once such a situation is detected, force readings from the second zeroing state may be used as calibration values that zero the sensor.

In some embodiments the probe is in proximity to another, second, probe. The inventors have found that changes in proximity between the probes may reduce the accuracy of the calibration values referred to above. In these embodiments the first probe may be assumed to be in the zeroing state if, in addition to the force condition described above, a measured value of the change in proximity is less than a predetermined proximity change threshold.

The inventors have found that, from measurements on actual cases using embodiments of the present invention, there is an extremely high probability of auto-zeroing the sensor when the sensor does not contact tissue. In addition, there is an extremely high probability of not auto-zeroing when the sensor does contact tissue.

System Description

In the following description, like elements in the drawings are identified by like numerals, and the like elements are differentiated as necessary by appending a letter to the identifying numeral.

Figure 1:
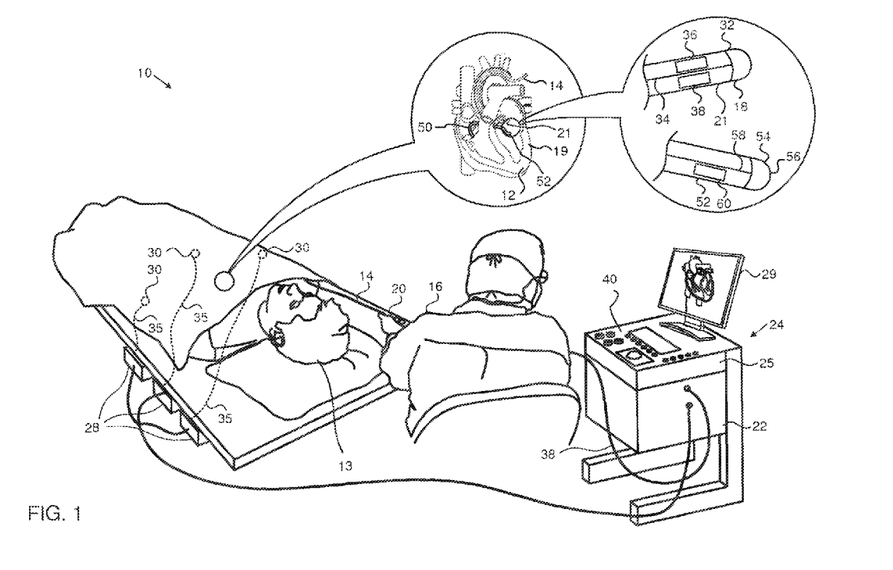
FIG. 1 is a pictorial illustration of a probe system for performing ablative procedures on a heart of a living subject, according to an embodiment of the invention.

Reference is now made to FIG. 1, which is a pictorial illustration of a probe system 10 for performing ablative procedures on a heart 12 of a living subject 13, according to an embodiment of the invention. The system comprises a probe 14, typically a catheter, which is percutaneously inserted by an operator 16 through the patient's vascular system into a chamber or vascular structure of the heart. The operator, who is typically a physician, brings the probe's distal tip 18 into contact with a heart wall 19 at an ablation target site. Optionally, electrical activation maps may then be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of system 10 is available as the CARTO® 3 System, available from Biosense Webster, Inc., 3333 Diamond Canyon Road, Diamond Bar, Calif. 91765.

Areas determined to be abnormal, for example by evaluation of the electrical activation maps, can be ablated by application of thermal energy, e.g., by passage of radiofrequency electrical current through wires in the probe to one or more electrodes at distal tip 18, which apply the radiofrequency energy to the myocardium. The energy is absorbed in the tissue, heating it to a point (typically about 50° C.) at which it permanently loses its electrical excitability. This procedure creates non-conducting lesions in the cardiac tissue, which disrupt the abnormal electrical pathway causing the arrhythmia. The principles of the invention can be applied to different heart chambers to treat many different cardiac arrhythmias.

Probe 14 typically comprises a handle 20, having suitable controls on the handle to enable operator 16 to steer, position and orient a distal end 21 of the probe as desired for the ablation. To aid the operator, the distal end of probe 14 contains a position sensor 38 that provides signals to a positioning processor 22, located in a console 24.

Ablation energy signals and other electrical signals can be conveyed to and from heart 12 through an electrode 32 located at distal tip 18 via a cable 34 to console 24. Electrode 32 may also be referred to herein as the ablation electrode. There may be other electrodes (not shown) located at the distal end that are used for ablation. Pacing signals and other control signals may be conveyed from the console through cable 34 and electrode 32, or via the other electrodes at the distal end, to the heart; these signals may be conveyed in parallel with any ablation energy signals, typically by using frequency multiplexing for the different signals.

Factors affecting the ablation generated by the ablation energy input to the tissue being ablated comprise, inter alia, the contact force applied to the tissue during the ablation process. In order to measure the contact force, the distal end of probe 14 comprises a force sensor 36. Force or pressure sensors that are suitable for use in a probe are well known in the art. For example, U.S. Patent Application Publications 2007/0100332 and 2009/0093806, whose disclosures are incorporated herein by reference, describe methods of sensing contact pressure between the distal tip of a probe and tissue in a body cavity using a force or pressure sensor embedded in the probe. However, force sensor 36 may comprise any other force or pressure sensor known in the art.

Wire connections 35 link the console with body surface electrodes 30 and other components of a positioning subsystem. Electrode 32 and body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near electrode 32.

Positioning processor 22 is an element of a positioning subsystem (of system 10) which measures location and orientation coordinates of probe 14, using position sensor 38.

In one embodiment, the positioning subsystem comprises a magnetic position tracking arrangement that determines the location and orientation of probe 14 by generating magnetic fields in a predefined working volume in the vicinity of the probe, using field generating coils 28. These fields are sensed by position sensor 38 and the sensed fields are used to determine location and orientation coordinates for the probe.

In console 24 an impedance module 40 is configured to measure an impedance of current flowing between ablation electrode 32 and body electrodes 30. In some cases measurements of the impedance may be used to estimate a location of electrode 32.

As noted above, probe 14 is coupled to console 24, which enables operator 16 to observe and regulate the functions of the probe. Console 24 includes a processor 25, preferably a computer with appropriate signal processing circuits, which operates system 10. Processor 25 is coupled to drive a monitor 29. The signal processing circuits typically receive, amplify, filter and digitize signals from probe 14, including signals generated by the above-noted sensors and a plurality of location sensing electrodes (not shown) located distally in the probe. The digitized signals are received and used by the console and the positioning subsystem to compute the location and orientation of probe 14 and to analyze the electrical signals from the electrodes.

Typically, during a medical procedure involving the measurement of contact force by force sensor 36, the output of the sensor drifts, even though the force on the sensor may be constant. Sensor 36 typically measures the magnitude and direction of the force, and the drift may be in one of these variables, or in both of them. The drift is typically caused by changes in parameters of physical elements associated with the sensor, such as gain changes of amplifiers and/or dimensional changes of parts of the sensor. The drift may be compensated for by zeroing the sensor, but the zeroing should only be performed when there is no contact between the distal tip of the probe and a solid object such as wall 19 of heart 12. Embodiments of the present invention detect periods when no such contact exists, and auto-zero sensor 36 during these periods.

In some embodiments a second probe 50, generally similar to probe 14, hereinbelow also termed the first probe, is located within heart 12 so that a distal end 52 of the second probe is in proximity to distal end 21 of the first probe. An electrode 54 is located at a distal tip 56 of the second probe, and the electrode is connected via a cable 58 to console 24. A position sensor 60, generally similar to position sensor 38, is also located within distal end 52 of the second probe.

In some cases, a change of the proximity of distal end 21 of the first probe to distal end 52 of the second probe alters readings of force sensor 36 in the first probe. The altered readings typically reduce the accuracy of, or even completely invalidate, any zero-force point derived from the readings during calibration of the sensor.

In cases of the presence of second probe 50, embodiments of the present invention use readings from force sensor 36 to estimate the proximity of the two distal ends, and to quantify the proximity numerically in a proximity index (PI) parameter. As is explained in more detail below, force sensor 36 is only zeroed if a change in the proximity index, ΔPI is less than a preset value.

Figure 2:
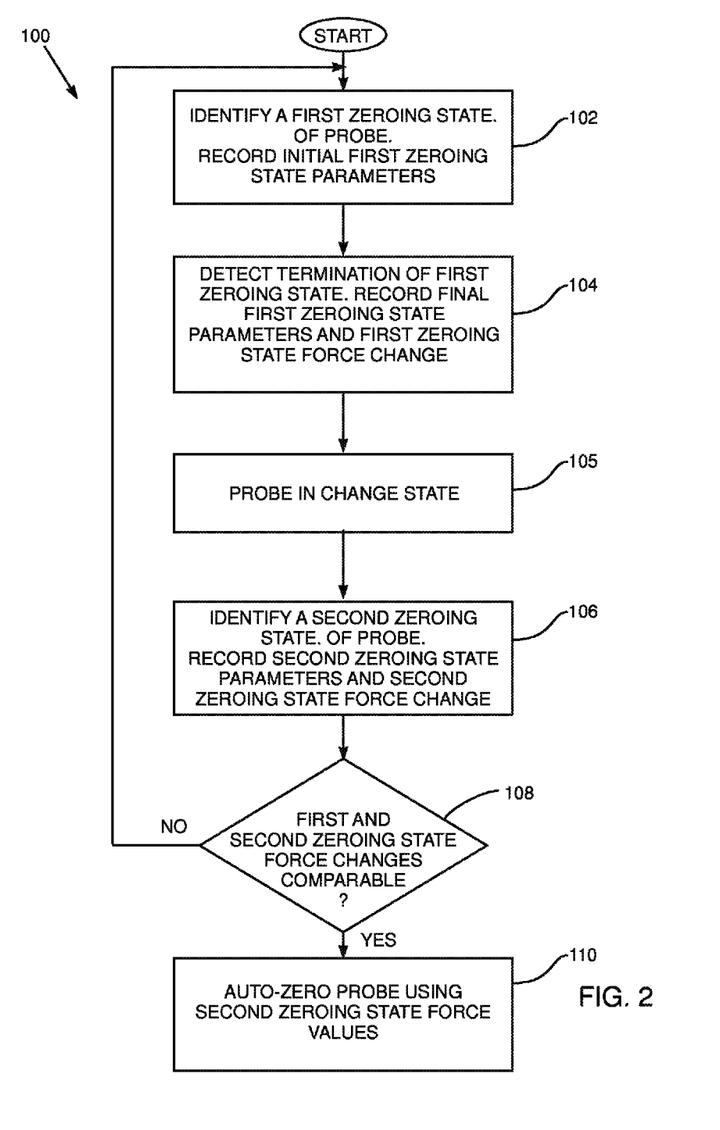
FIG. 2 is a first flowchart of steps followed by a processor of the probe system, according to an embodiment of the invention.
Figure 3:
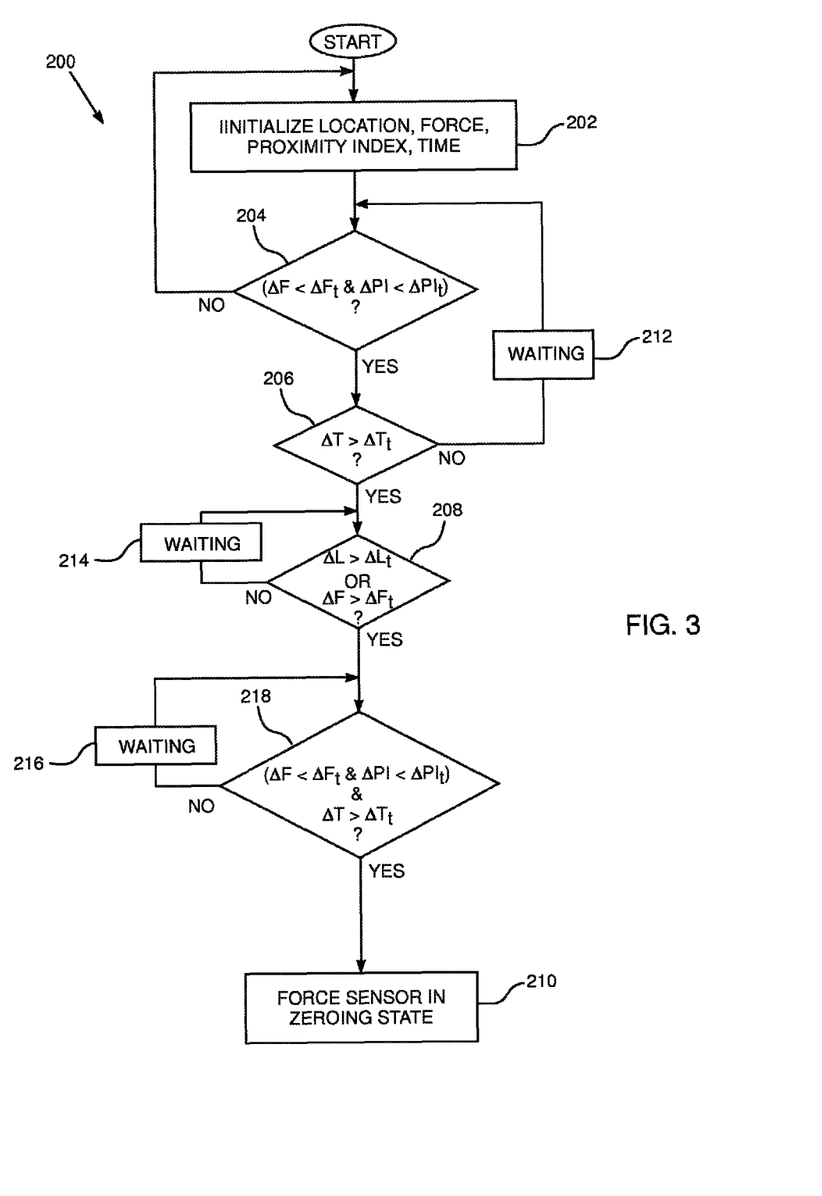
FIG. 3 is a second flowchart of steps followed by the processor, according to an embodiment of the present invention.

FIG. 2 is a first flowchart 100 of steps followed by processor 25 and FIG. 3 is a second flowchart 200 of steps followed by the processor, in auto-zeroing sensor 36, according to embodiments of the present invention. Flowchart 100 is a "high-level" flowchart of the steps followed by the processor in determining when, and with what values, sensor 36 of the first probe is to be auto-zeroed. Flowchart 100 assumes that sensor 36 is in or is not in a "zeroing state." Flowchart 200 is a "low-level" flowchart, providing the steps used by processor 25 in deciding when sensor 36 is in a zeroing state.

Except where otherwise stated, the descriptions for the two flowcharts assume that second probe 50 is also present in heart 12.

To perform the steps of the two flowcharts, processor 25 uses values of force, proximity index, and location that are measured for distal tip 18. The force sensor is able to measure both the magnitude and direction of the force, but for simplicity in the following description, only the magnitude of the force is considered. Those having ordinary skill in the art will be able to adapt the description, mutatis mutandis, to account for changes in the direction of the force, typically by calculating the magnitude of the change of force vector.

For both flowcharts, the processor uses predetermined threshold values for a force change, a proximity index change, a location change, and a time period. The force, proximity index, and location changes, and the time period threshold values are respectively represented by the symbols $\Delta F_t$, $\Delta PI_t$, $\Delta L_t$, and $\Delta T_t$. In a disclosed embodiment $\Delta F_t=1$ g, $\Delta PI_t=1.5$, $\Delta L_t=10$ mm, and $\Delta T_t=1000$ ms.

Processor 25 typically runs the two flowcharts in parallel.

For high level flowchart 100, in a first zero identifying step 102, processor 25 uses measurements of time, force, proximity index and location to identify that force sensor 36 is in a zeroing state. Flowchart 200 provides details of how the measurements are used to determine of the sensor is in a zeroing state. At the beginning of step 102, the processor saves initial values of time $T_{init}$, force $F_{init}$, proximity index $PI_{init}$, and location $L_{init}$. While in step 102, the processor continues to acquire values of the time, the force, the proximity index, and the location. A zeroing state for the force sensor corresponds to a state where values of the time, force, proximity index and location for the sensor indicate that the sensor distal tip of the probe is not in contact with any solid surface, and that the proximity of the two probe distal ends has not changed significantly. However, in a zeroing state there is typically drift in the signal output by the force sensor. As is shown in flowchart 200, the zeroing state corresponds to, for at least predetermined time period $\Delta T_t$, the force registered by the force sensor changing by less than predetermined force change threshold value $\Delta F_t$, the distal end moving by more than predetermined distance $\Delta L_t$, and the proximity index changing by less than predetermined proximity index change threshold $\Delta I_t$.

In a termination step 104, the processor uses measurements of the force and of the location to establish that the force sensor is no longer in its zeroing state. The processor invokes termination step 104 if either the force change measured by sensor 36 exceeds $\Delta F_t$ or if the location of distal tip 18 changes by more than $\Delta L_t$. At this point the processor saves current values of the force $F_{current}$ and calculates a first zeroing step force change $\Delta F_1$ according to equation (1):

$$\Delta F_1 = |F_{current} - F_{init}| \quad (1)$$

After completing termination step 104, in a change state step 105 the probe enters a change state, where it is no longer in a zeroing state.

In a second zero identifying step 106, processor 25 identifies that force sensor 36 is in a second zeroing state, substantially repeating the procedure of step 102. While in the second zeroing state, the processor calculates, on a continuing basis, updated values of force changes, $\Delta F_2$, using an initial force saved on entering step 106 and an equation corresponding to equation (1).

In a comparison step 108, the processor compares the changes of values of the force of zeroing state step 106 with those saved in step 104. I.e., the processor compares values of $\Delta F_1$ and $\Delta F_2$. Providing that the difference of the force changes is within a predetermined limit, typically the predetermined force change threshold $\Delta F_t$, in an auto-zero step 110 the processor is able to auto-zero the sensor, typically by using the most recent values acquired from the force sensor in step 106 as zero-point values for the sensor. In one embodiment the zero-point values are an average of the most recent signal values taken over a predetermined time period, such as 1 s.

If in comparison step 108 the difference of the force changes is not within its predetermined limit, the flowchart returns to step 102, and the processor reiterates the steps of the flowchart.

Review of flowchart 100 shows that, for each iteration of the flowchart, in steps 102 and 104 the processor generates and saves a set of values $\{Z_n\}=\{T_{init}, T_{current}, F_{init}, F_{current}, PI_{init}, PI_{current}, L_{init}, L_{current}\}_n$, where n is the number of the iteration. In some embodiments, in step 108, the processor compares force change values found in step 106 with all of the saved force change values of previous iterations. If any one of the comparisons is valid, then the comparison step 108 is assumed to return positive and the processor uses the values in the second zeroing step to auto-zero the force sensor.

FIG. 3 is flowchart 200, which comprises steps performed by processor 25 in deciding if force sensor 36 is in a zeroing state. In some cases, the force sensor may be in an intermediate state, as explained below. In making its decisions, the processor uses threshold values $\Delta F_t$, $\Delta PI_t$, $\Delta L_t$, and $\Delta T_t$, referred to above.

For the steps of the flowchart, which mainly comprises comparisons, processor 25 performs each of the steps on a continuing basis so that the sequence of steps is performed reiteratively as a loop. For each loop iteration there is a new value of time, and typically new values of force, location or proximity index. In some embodiments flowchart 200 is implemented as a state machine. From the flowchart description herein, such a state machine will be apparent to those having ordinary skill in the art.

In an initial state step 202 the processor saves initial values of time $T_{init}$, force $F_{init}$, proximity index $PI_{init}$, and location $L_{init}$.

In a first comparison step 204, the processor measures a current value of the force $F_{current}$ and a current value of the proximity index $PI_{current}$. Using the initial force and proximity index values from step 202, the processor calculates changes in values of force and proximity index according to equations (2):

$$\Delta F = |F_{current} - F_{init}| \brace \Delta PI = |PI_{current} - PI_{init}|} \quad (2)$$

The processor then determines if the expression in expression (3) returns true or false:

$$\Delta F < \Delta F_t \text{ and } \Delta PI < \Delta PI_t \quad (3)$$

The force comparison and the proximity index comparison are preliminary tests which are typically true if the distal tip is not in contact with wall 19 of the heart, and if the proximity index has not changed appreciably.

If expression (3) returns true, then the flowchart continues with further comparisons, starting with a second comparison 206: $\Delta T > \Delta T_t$. If expression (3) returns false, the flowchart returns to initial step 202.

If second comparison 206 returns false, then force sensor 36 is in a first waiting state 212, waiting for the first comparison to have been true for threshold time $\Delta T_t$, and the flowchart returns to first comparison 204.

If second comparison 206 returns true, the flowchart continues to a third comparison 208, $\Delta L > \Delta L_t$ OR $\Delta F > \Delta F_t$. In comparison 208 the processor respectively checks if the sensor has moved by more than the threshold distance $\Delta L_t$, or if the force has changed by more than the threshold force $\Delta F_t$.

If comparison 208 returns false, then force sensor 36 is in a second waiting state 214 where the force sensor is waiting to move more than the threshold distance $\Delta L_t$ or for the force change to exceed the threshold force $\Delta F_t$.

If comparison 208 returns true, the flowchart continues to a fourth comparison 218, wherein the initial values $F_{init}$ and proximity index $PI_{init}$ are updated to the respective values when the processor enters the comparison.

In comparison 218 the processor checks that, over a time period greater than the time threshold $\Delta T_t$, the force has changed by less than the force threshold $\Delta F_t$ and the proximity index has changed by less than the proximity index threshold $\Delta PI_t$.

If comparison 218 returns true, the force sensor is in a zeroing state 210.

If comparison 218 returns false, the force sensor is in a third waiting state 216, where the sensor is waiting for comparison 218 to become true.

As is apparent from comparison 218, the force sensor is in zeroing state 210 if, for at least a predetermined time period $\Delta T_t$, the force registered by the force sensor changes by less than predetermined force threshold value $\Delta F_t$ and the proximity index changes by less than predetermined proximity index change threshold $\Delta PI_t$. The condition of comparison 218 typically only holds if the distal tip does not contact wall 19 of the heart and if there has been no appreciable proximity index change.

The description above for flowcharts 100 and 200 has assumed the presence of probe 50, and that the distal ends of probes 14 and 50 may be in proximity to each other. Those having ordinary skill in the art will be able to adapt the description, mutatis mutandis, for the case when there is no probe distal end proximate to the distal end of probe 14. Such adaptation may comprise, for example, equating $\Delta PI$, in the conditions above regarding the proximity index, to zero.

Figure 4:
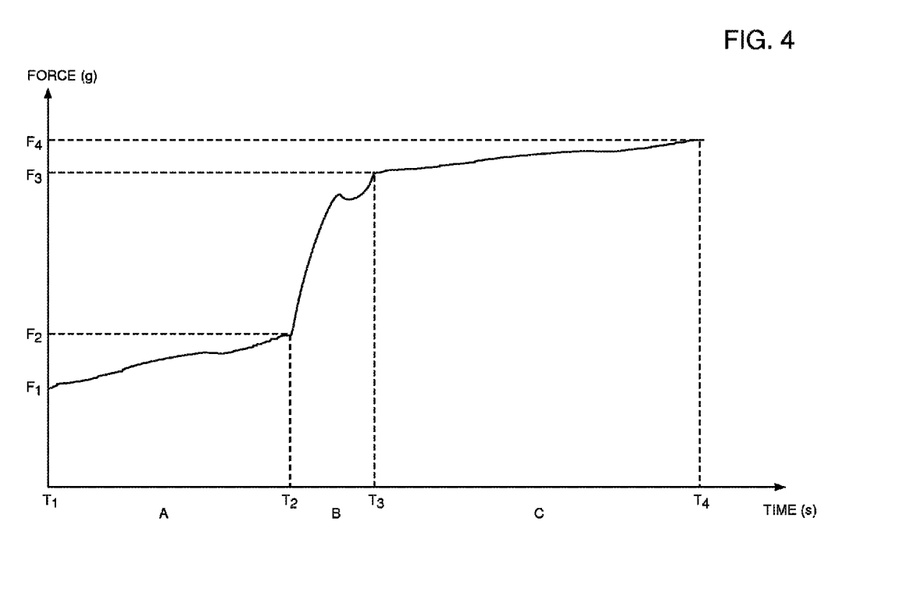
FIG. 4 is a schematic graph of force magnitude vs. time for the probe system, according to an embodiment of the present invention.

FIG. 4 is a schematic graph of force magnitude vs. time, according to an embodiment of the present invention. The graph illustrates values of time and the force magnitude, derived from a vectorial force, as measured for distal tip 18.

While the time and the force are being measured, location and proximity values for the distal tip are also measured, but for simplicity graphs of these values vs. time are not shown. The force magnitude is measured in grams (g), and the time is measured in seconds (s). The graph is divided into three time periods, $T_1$-$T_2$, $T_2$-$T_3$, and $T_3$-$T_4$, also respectively referred to herein as periods A, B and C.

Considering period A, and applying values from the graph of this period to flowchart 200, if all of the conditions of expression (4) are assumed to be true, then at time $T_2$ the force sensor is in zeroing state 210.

$$\left. \begin{array}{l} F_2 - F_1 < \Delta F_t \\ T_2 - T_1 > \Delta T_t \\ \Delta PI_A < \Delta PI_t \\ \Delta L_A > \Delta L_t \end{array} \right\} \quad (4)$$

The first two comparisons in expression (4) are illustrated in the graph; the third and fourth comparisons are from measured proximity index and location changes, $\Delta PI_A$ and $\Delta L_A$, during period A.

Similarly for period C, if all of the conditions of expression (5) are assumed to be true, then at time $T_4$ the force sensor is in zeroing state 210.

$$\left. \begin{array}{l} F_4 - F_3 < \Delta F_t \\ T_4 - T_3 > \Delta T_t \\ \Delta PI_C < \Delta PI_t \\ \Delta L_C > \Delta L_t \end{array} \right\} \quad (5)$$

The graph for periods A and C illustrate the case where distal tip 18 is not in contact with wall 19.

Considering period B, if $F_3$-$F_2$>$\Delta F_t$ then the force sensor is not in a zeroing state. The graph for period B illustrates the case where distal tip 18 is in contact with wall 19.

The situation illustrated by the graph, of a first and second zeroing state separated by a period in time where there is a change of force greater than the threshold force, may be applied to flowchart 100. Steps 102, 104, 105, and 106 all apply. Assuming comparison 108 is valid, then in step 110 the probe is auto-zeroed at time $T_4$ using values from time period C.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method, comprising:
    inserting a probe into a cavity in a body of a subject, the probe configured to measure and transmit control forces and location coordinates to one or more processors, the one or more processors being responsive to a plurality of instructions stored in a non-transitory computer readable medium, which when executed, cause the one or more processors to:
    obtain, by the one or more processors, in a first period, from a force sensor in the probe, first readings indicative of a first change in measured contact forces between the probe and the cavity by less than a predetermined limit over at least a predetermined interval of time, the measured contact forces comprising at least one of the magnitudes of the contact forces and the directions of the contact forces;
obtain, by the one or more processors, in a second period after the first period, second readings from the force sensor when one condition is met from a set of conditions consisting of:
the second readings having changed in at least one of magnitude of the contact forces and direction of the contact forces by more than a predetermined force threshold in the second period; and
location coordinates of the probe having changed by at least a predetermined location change threshold in the second period;
obtain, by the one or more processors, from the force sensor, in a third period after the second period, third readings indicative of a second change in the measured contact forces between the probe and the cavity by less than predetermined limit over at least the predetermined interval of time; and
calibrate, by the one or more processors, a zero-force point for the force sensor according to the third readings.

2. The method according to claim 1, wherein the plurality of instructions, when executed, further cause the one or more processors to:
receive in the first period first location signals indicative of a first location change for the probe by more than a predetermined location threshold; and
receive in the third period second location signals indicative of a second location change for the probe by more than the predetermined location threshold.

3. The method according to claim 1, wherein the probe comprises a first probe, and wherein the plurality of instructions, when executed, further cause the one or more processors to:
insert a second probe into the cavity in proximity to the first probe;
receive in the first period first signals indicative of a first change in a measured value of the proximity by less than a predetermined proximity change threshold; and
receive in the third period second signals indicative of a second change in the measure value of the proximity by less than the predetermined proximity change threshold.

4. The method according to claim 1, wherein the plurality of instructions, when executed, further cause the one or more processors to receive the first signals and the second signals from the force sensor.

5. The method according to claim 1, wherein the probe comprises a magnetic field sensor, and wherein the plurality of instructions, when executed, further cause the one or more processors to measure the location coordinates of the probe in response to magnetic fields sensed by the sensor.

6. The method according to claim 1, wherein the probe comprises an electrode and wherein the plurality of instructions, when executed, further cause the one or more processors to measure the location coordinates in response to an impedance of current flowing through the electrode.

7. The method according to claim 1, wherein the predetermined limit of the measured contact forces is equal to the predetermined force threshold.

8. An apparatus, comprising:
a probe configured to be inserted into a cavity in a body of a subject;
a force sensor located within the probe;
a console having one or more processors; and
a non-transitory computer readable medium storing a plurality of instructions, which when executed, cause the one or more processors to:
obtain, by the one or more processors from the force sensor, in a first period, first readings indicative of a first change in measured contact forces between the probe and the cavity by less than a predetermined limit over at least a predetermined interval of time, the measured contact forces comprising at least one of magnitudes of the contact forces or directions of the contact forces,
obtain, by the one or more processors, in a second period after the first period, second readings from the force sensor when one condition is met from a set of conditions consisting of:
the second readings having changed in at least one of magnitude of the contact forces and direction of the contact forces by more than a predetermined force threshold in the second period, and
location coordinates of the probe having changed by at least a predetermined location change threshold in the second period,
obtain, by the one or more processors from the force sensor, in a third period after the second period, third readings indicative of a second change in the measured contact forces between the probe and the cavity by less than the predetermined limit over at least the predetermined interval of time, and
calibrate, by the one or more processors, a zero-force point for the force sensor according to the third readings.

9. The apparatus according to claim 8, and comprising a position sensor located within the probe, and wherein the instructions, when executed, further cause the one or more processors to:
receive in the first period first location signals from the position sensor indicative of a first location change for the probe by more than a predetermined location threshold; and
receive in the third period second location signals from the position sensor indicative of a second location change for the probe by more than the predetermined location threshold.

10. The apparatus according to claim 8, wherein the probe comprises a first probe, the apparatus further comprising a second probe configured to be inserted into the cavity in proximity to the first probe, and wherein the processor is configured:
to receive in the first period first signals indicative of a first change in a measured value of the proximity by less than a predetermined proximity change threshold; and
to receive in the third period second signals indicative of a second change in the measured value of the proximity by less than the predetermined proximity change threshold.

11. The apparatus according to claim 8, wherein the instructions, when executed, further cause the one or more processors to receive the first signals and the second signals from the force sensor.

12. The apparatus according to claim 8, wherein the probe comprises a magnetic field sensor, and wherein the instructions, when executed, further cause the one or more to measure the location coordinates in response to magnetic fields sensed by the sensor.

13. The apparatus according to claim 8, wherein the probe comprises an electrode, and wherein the processor is configured to measure the location coordinates in response to an impedance of current following through the electrode.

14. The apparatus according to claim 8, wherein the predetermined limit of the measured contact forces is equal to the predetermined force threshold.

* * * * *